United States Patent
Bucala et al.

(10) Patent No.: US 6,255,046 B1
(45) Date of Patent: Jul. 3, 2001

(54) INDUCIBLE PHOSPHOFRUCTOKINASE AND THE WARBURG EFFECT

(75) Inventors: Richard J. Bucala, Cos Cob, CT (US); Jason A. Chesney; Robert A. Mitchell, both of New York, NY (US)

(73) Assignee: The Picower Institute for Medical Research, Manhasset, NY (US)

( * ) Notice: Subject to any disclaimer, the term of this patent is extended or adjusted under 35 U.S.C. 154(b) by 0 days.

(21) Appl. No.: 09/183,846

(22) Filed: Oct. 30, 1998

Related U.S. Application Data

(63) Continuation-in-part of application No. 08/961,578, filed on Oct. 31, 1997.

(51) Int. Cl.[7] .......................... C12Q 1/00; G01N 33/573; G01N 33/53
(52) U.S. Cl. ................ 435/4; 435/7.4; 435/7.72
(58) Field of Search ........................... 435/7.1, 7.2, 7.23, 435/7.4, 7.71, 7.72, 69.2, 4; 436/64

(56) References Cited

FOREIGN PATENT DOCUMENTS

WO 97/15674 * 5/1997 (WO).

* cited by examiner

*Primary Examiner*—Susan Ungar
*Assistant Examiner*—Gary Nickol
(74) *Attorney, Agent, or Firm*—Piper Marbury Rudnick & Wolfe LLP; Steven B. Kelber

(57) ABSTRACT

There is disclosed a cancer malignancy diagnostic assay comprising obtaining a sample of a body fluid or tissue, performing a sequence identity assay to look for the presence of iPFK-2 specific sequences; an anticancer pharmaceutical composition comprising a specific antisense oligonucleotide to the inventive isolated iPFK-2 sequence and a pharmaceutically acceptable oligonucleotide carrier; and a method for finding therapeutically active anti-cancer compounds comprising screening compounds for activity to inhibit iPFK-2, preferably kinase activity.

2 Claims, 14 Drawing Sheets

FIG. 1

INDUCIBLE PHOSPHOFRUCTOKINASE AND THE WARBURG EFFECT

CROSS REFERENCE TO RELATED APPLICATION

This patent application is a continuation-in-part from U.S. patent application Ser. No. 08/961,578 filed Oct. 31, 1997.

TECHNICAL FIELD OF THE INVENTION

The present invention provides a novel phosphofructokinase isozyme (iPFK-2) that is preferentially transcribed and translated in tumor cells. The discovery of this isozyme, together with its function, led to the discovery of its use as a diagnostic target, as a drug screening target, and antisense compounds that inhibit its translation in cellular cytosol as an anti-tumor treatment.

BACKGROUND OF THE INVENTION

The glycolytic pathway is a fundamental anaerobic pathway for sugar metabolism in eukaryotic cells. Glycolysis has a dual role, to degrade sugars to generate energy (ATP) and to provide building blocks for synthetic reactions. The rate of conversion of glucose into pyruvate is regulated to meet these two major cellular needs. In glycolysis, the enzymes hexokinase, phosphofructokinase and pyruvate kinase catalyze irreversible reactions and are regulated enzymes for control points in glycolysis. The enzymes are regulated by reversible binding of allosteric effectors, by covalent modification and by transcriptional control to meet changing metabolic needs. Of the three control enzymes, phosphofructokinase is the most important control point in mammalian glycolysis.

In 1930, Warburg pointed out that tumors have a high rate of anaerobic glycolysis and that they do not show a decreased glycolytic rate at relatively high $O_2$ concentrations. This loss of regulatory control (i.e., the Pasteur effect) has come to be called the Warburg effect. Supplying tumor cells with glucose results in an inhibition of oxygen consumption, which magnifies the dependence on glucose for energy. Other cellular types do not normally show this effect since they maintain respiration from other substrates even in the presence of glucose. The question of why rapidly growing tumors have a marked tendency to convert the glycolytically-generated pyruvate to lactic acid in the cytosol instead of transporting into the mitochondria for total oxidation has puzzled biochemists for years. The physiologic consequence of this altered metabolic behavior are clear. Tumor tissue generates a high degree of metabolic inefficiency in the host, through an enhanced operation of energy-wasting processes, such as the Cori cycle between the tumor and the liver. As a result of the high glycolytic rate, a large amount of pyruvate is generated, together with an increase in the cytosolic NADH/NAD+ ratio, which favors the reduction of pyruvate to lactate through the action of lactate dehydrogenase. This is also supported by the low mitochondrial content of tumor cells which hampers the possibility of dissipating NADH through the action of the electron transfer chain and the low levels of NADH- shuttle systems found in a great number of tumors. The tumor cell becomes a lactate exporter in a similar way to some muscular fibers in anoxic situations. Although the precise role of the enhanced Cori cycle in tumor-bearing states is not fully determined, it adds inefficiency to the host in a way that, instead of ATP formation of 36–38 molecules during the complete oxidation of glucose to $CO_2$, a net loss of 4 ATPs can be expected when two three-carbon molecules are converted to one molecule of glucose.

A distinctive metabolic environment of cancer-bearing individuals has been described (Argiles and Azcón-Bieto, *Mol. Cell. Biochem.* 81:3–17, 1988). Tumor invasion upon a host has been metabolically characterized by a reduction of the metabolic efficiency of the host, muscular protein depletion, increased gluconeogenesis, and uncoupling of oxidative phosphorylation. The net result is an energy imbalance leading to cachexia and eventual starvation.

SUMMARY OF THE INVENTION

The present invention provides a cancer malignancy diagnostic assay comprising obtaining a sample of a body fluid or tissue (including, for instance, a sample of tumor tissue), and performing a sequence identity assay to look for the presence of iPFK-2 specific sequences (SEQ ID NO.: 11). Preferably, the sequence identity assay is selected from the group consisting of PCR (polymerase chain reaction) assays, ELISA immunologic assays, hybridization assays, and combinations thereof. The present invention further provides an anticancer, anti-inflammatory and cachexia pharmaceutical composition comprising a specific antisense oligonucleotide to the inventive isolated iPFK-2 sequence and a pharmaceutically acceptable oligonucleotide carrier. Preferably, the antisense oligonucleotide is a 15–50 base oligonucleotide incorporating an oligonucleotide sequence selected from the group consisting of: 5'-CCAACGGCATCTTCGCGGCT-3' [SEQ ID NO: 2], 5'-GTCAGTTCCAACGGCATCTT-3' [SEQ ID NO: 4], and combinations thereof. The present invention further provides a therapeutic agent screening assay to screen for compounds having anti-tumor activity, comprising: (a) obtaining recombinant iPFK-2 having activity that forms fructose 2,6-bisphosphate from fructose 6-phosphate substrate; (b) adding candidate drug at various concentrations or no-drug control vehicle; and (c) assaying for fructose 2,6-bisphosphate as a measure of enzymatic activity. Preferably, the product assay is conducted by means of an enzymatic assay.

The present invention further provides a recombinant iPFK-2 polypeptide expressed by the cDNA sequence provided in SEQ ID NO. 11. The use of the iPFK-2 polypeptide, with known antibody techniques, including known monoclonal antibody techniques, further provides antibodies that specifically bind to iPFK-2. Preferably, such antibodies are monoclonal antibodies.

BRIEF DESCRIPTION OF THE FIGURES

FIG. 1 shows the predicted amino acid sequence and alignment of the novel iPFK-2 cDNA with PFK-2 sequences deduced from a human placental (Sakai, Kato, Fukusawa et al., *J. Biochem.* 119:506–511, 1996) and a human liver (Lange and Pilkis, *Nuc. Acids Res.* 18:3652, 1990) cDNA clone. Boxed residues indicate identity.

FIG. 2A shows a RT-PCR analysis. FIG. 2B shows a Northern blot analysis. FIG. 2C shows a Western blot analysis, wherein the anti-iPFK-2 antiserum used in the right panel was pre-absorbed with the iPFK-2-specific peptide against which the antiserum was raised.

FIG. 3A shows a Northern blot analysis of various human cancer cell lines. FIG. 3B shows a RT-PCR analysis of K-562 cells for β-actin, iPFK-2 and human liver PFK-2.

FIG. 4A shows a Western blot analysis of the iPFK2 antagonist activity of the antisense oligonucleotide. FIG. 4B shows a fructose-2,6-bisphosphate assay of the iPFK2 antagonist activity of the antisense oligonucleotide(AS) versus the sense (S) sequence. FIG. 4C shows a 5-phosphoribosyl 1-pyrophosphate assay and a K562 cell proliferation assay of the iPFK2 antagonist activity of the antisense oligonucleotide(AS) versus the sense (S) sequence.

DETAILED DESCRIPTION OF THE INVENTION

Figure 2A:
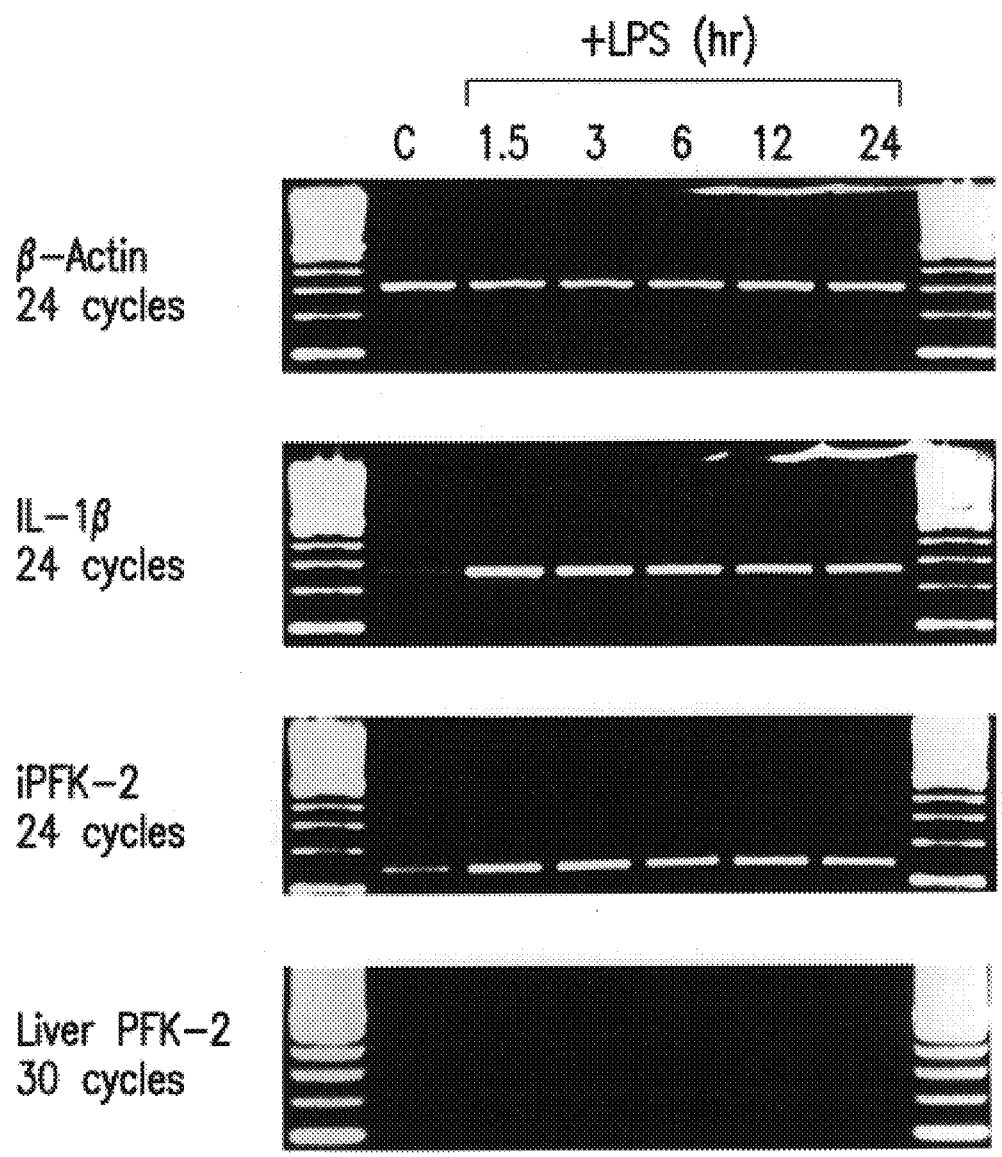
FIGS. 2A–C shows that LPS induces peripheral blood monocytes to rapidly express iPFK-2 mRNA and protein.

The present invention provides a cancer malignancy diagnostic assay comprising obtaining a sample of a body or tumor fluid or tissue, and performing a sequence identity assay to look for the presence of iPFK-2 specific sequences. Preferably, the sequence identity assay is selected from the group consisting of PCR (polymerase chain reaction) assays, ELISA immunologic assays, hybridization assays, and combinations thereof. The present invention further provides an anticancer pharmaceutical composition comprising an antisense oligonucleotide specific to the inventive isolated PFK-2 sequence and a pharmaceutically acceptable oligonucleotide carrier. Preferably, the antisense oligonucleotide is selected from a 15–50 base oligonucleotide incorporating an oligonucleotide sequence selected from the group consisting of ): 5'-CCAACGGCATCTTCGCGGCT-3' [SEQ ID NO: 2], 5'-GTCAGTTCCAACGGCATCTT-3' [SEQ ID NO: 4], and combinations thereof.

The present invention further provides a recombinant iPFK-2 polypeptide expressed by the cDNA sequence provided in SEQ ID NO. 11. The use of the iPFK-2 polypeptide, with known antibody techniques, including known monoclonal antibody techniques, further provides an antibody that specifically binds to iPFK-2. Preferably, this antibody is a monoclonal antibody.

The present invention further provides an isolated cDNA sequence encoding an inducible human phosphofructokinase-2 (iPFK-2) enzyme. The cDNA sequence is listed as SEQ ID NO 11. SEQ ID NO. 11 provides a bolded start and stop codon of the coding region. Further, there are underlined base pairs at the C terminal region of the coding region that provide additional amino acids not found in any other PFK-2 isotypes. The inventive iPFK-2 cDNA sequence is useful for producing recombinant iPFK-2 polypeptide, for designing antisense oligonucleotides, and for transfecting cells (both prokaryotic and eukaryotic) to produce recombinant iPFK-2 and fragments thereof. The recombinant iPFK-2 polypeptide, having PFK-2 enzymatic activity, is useful for screening for inhibitors having therapeutic activity as anticancer agents specifically against the inventive inducible iPFK-2 isoform. Anticancer therapeutic activity can be attributable to iPFK-2 inhibitors because a novel, AU-rich early response gene is required for leukemia growth. This gene appears to be the inducible iPFK-2 gene, the gene product of which is most prevalent in tumor cells.

The present invention further provides an isolated cDNA sequence encoding an inducible human phosphofructokinase-2 (iPFK-2) isozyme. The examples below detail the efforts that led to the isolation, purification and expression of this isozyme. The isolated isozyme sequence was found to be preferentially expressed in tumor cells and lead to increased glycolytic activity.

The invention is based upon the identification and understanding of a novel gene for PFK-2/FBPase (6-phosphofructo-2-kinase (PFK-2)/fructose-2,6-biphosphophatase (FBPase)) or "iPFK-2" that is induced by pro-inflammatory stimuli and which is distinguished from other similar genes encoding PFK-type enzymes by the presence of multiple copies of an AUUUA mRNA instability motif in its 3'-untranslated end. This AU-rich element is characteristic of mRNAs encoding several inflammatory cytokines (e.g., TNFα, IL-1, IFN-γ, and GM-CSF) and oncoproteins (e.g., c-Fos, c-Myc, and c-Sis) (Greenberg and Belasco, in *Control of Messenger RNA Stability*, Belasco and Brawerman eds., pp. 199–218, Academic Press, New York, 1993). Data presented herein shows that iPFK-2 is expressed constitutively in several human cancer cell lines and was found to be essential for tumor cell growth in vivo. Inhibiting the level of iPFK-2 protein expression (through the use of antisense antagonists) decreased intracellular levels of 5-phosphoribosyl-1-pyrophosphate (PRPP), an important precursor for purine and pyrimidine biosynthesis. Accordingly, iPFK-2 is an important regulatory isoenzyme that appears to be essential for tumor growth, whose antagonists have important anti-cancer therapeutic activity, and provides an explanation for long-standing observations concerning the apparent coupling of glycolysis and cancer cell proliferation.

Figure 1:
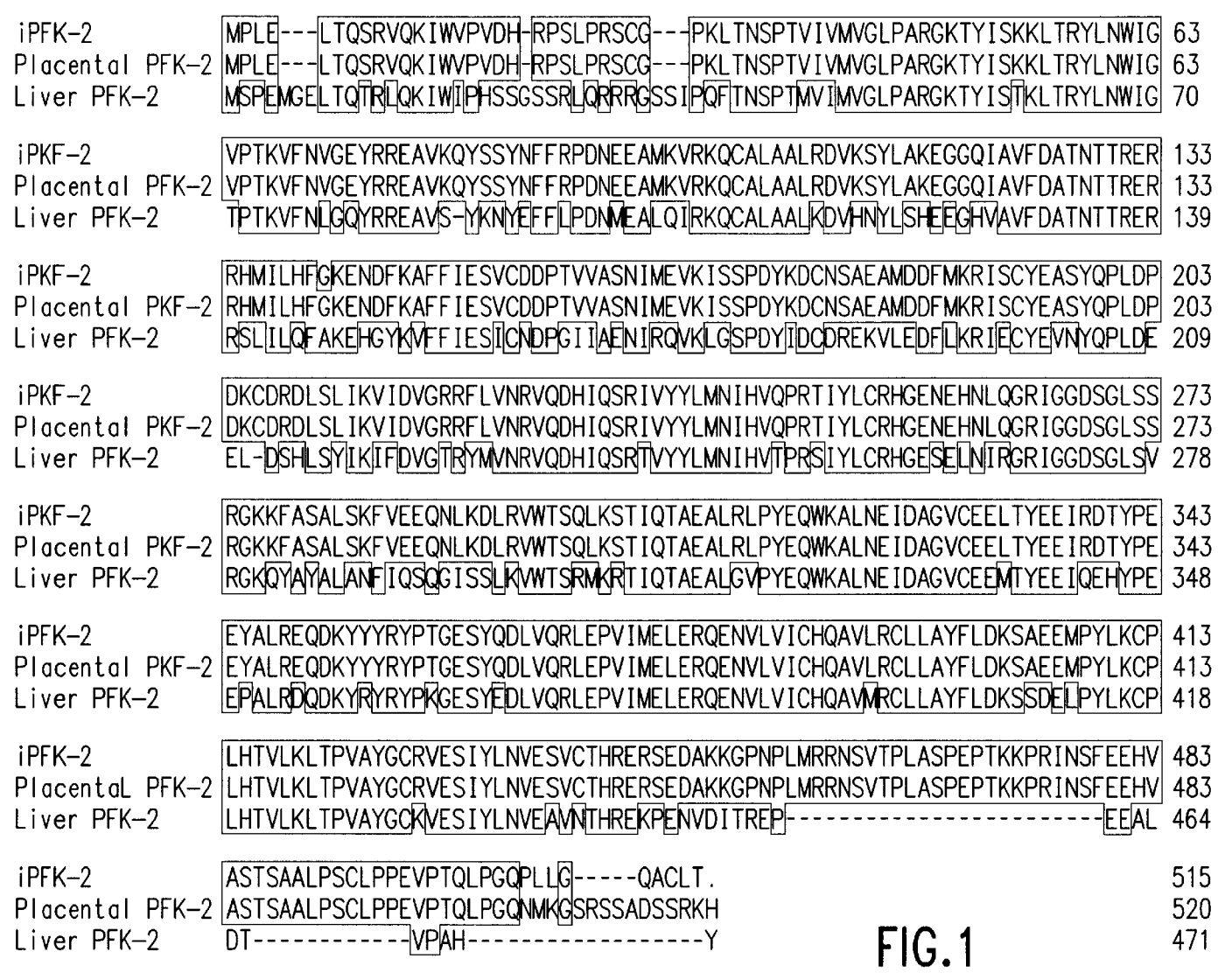

The mRNAs of several cytokines and proto-oncogenes that are members of early response gene families have been noted to contain the sequence motif AUUUA in their 3' untranslated region (3'UTR). This AU-rich element confers instability to the mRNA molecule and plays a role in regulating its physiologic half life (Caput et al., *Proc. Natl. Acad. Sci. USA* 83:1670–1674, 1986; and Shaw et al., *Cell* 46: 659–667, 1986). An expressed sequence tag (EST) database was searched for cDNA sequences containing conserved AUUUA sequence motifs. One AU-rich EST, unrelated to previously described genes, was identified and the complete cDNA was cloned and sequenced. The DNA sequence of this novel gene was found to share 29% identity with human liver PFK-2 (FIG. 1), which does not contain AU-rich elements. The predicted amino acid sequence showed 69% identity and extensive conservative substitutions (FIG. 1) (Lange and Pilkis, *Nucl. Acids Res.* 18:3652, 1990).

Figure 2B:
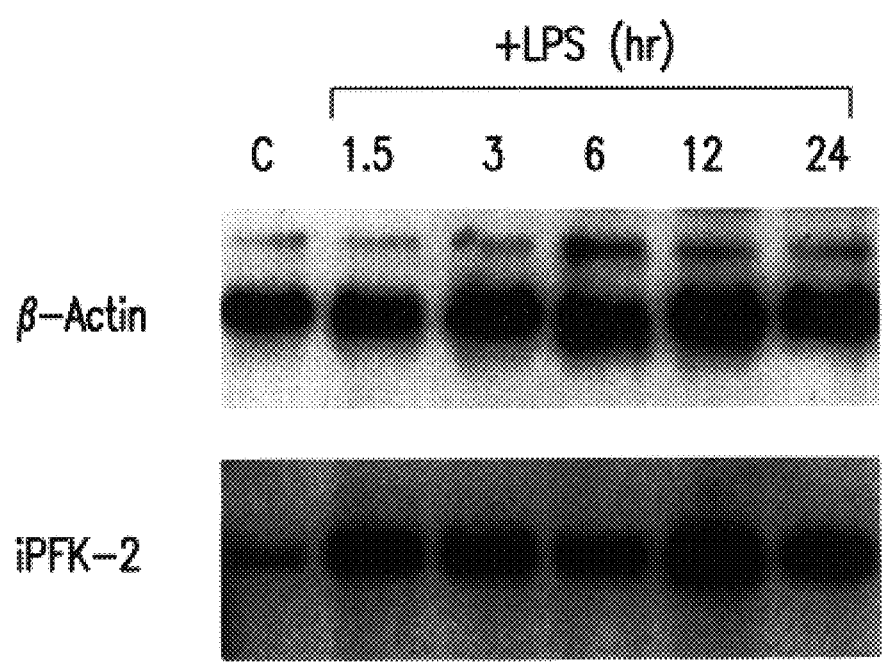
Figure 2C:
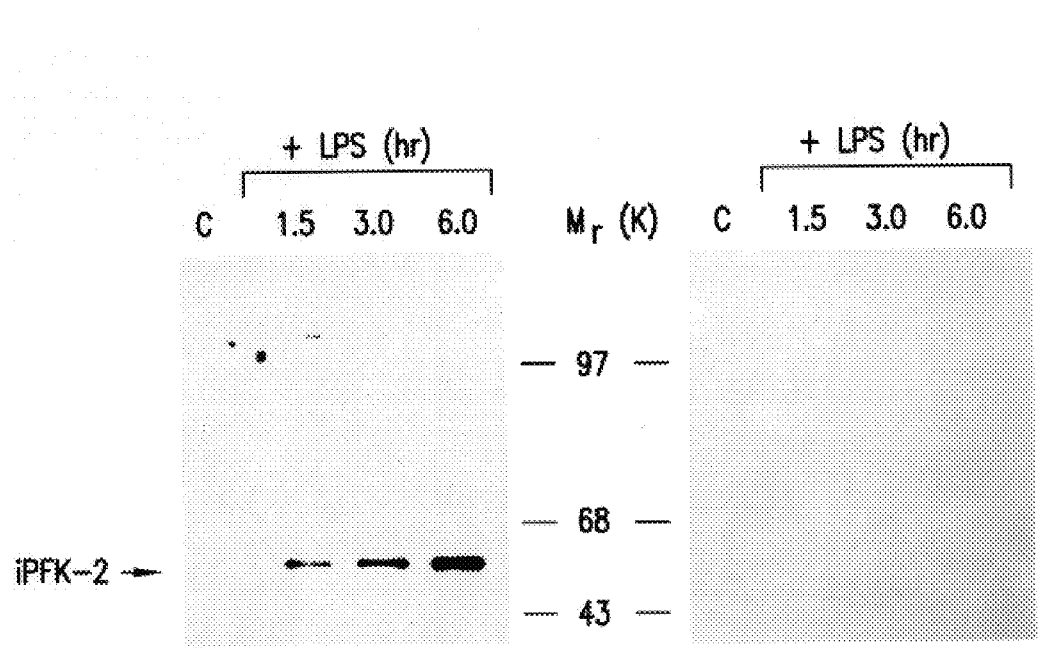

The expression of many proto-oncogenes and cytokines bearing the AUUUA motif increases in cells as a consequence of mitogenic or pro-inflammatory stimulation. Thus, only very low levels of iPFK-2 expression were detected by Northern blotting of normal human tissues (i.e., heart, brain, placenta, lung, liver, skeletal muscle, kidney, pancreas, spleen and lymph node). Northern analysis of human monocytes stimulated with lipopolysaccharide (LPS), by contrast, showed that the expression of this novel iPFK-2 gene was rapidly induced (FIG. 2A), hence the term "iPFK-2." The induction and increase in the level of iPFK-2 expression was similar to that which was observed for the cytokine IL-1β (which also contains AU-rich elements) (FIG. 2B). The expression of the liver (constitutive) isoform of PFK-2 was unaffected by LPS stimulation. Induction of iPFK-2 mRNA was accompanied by a corresponding increase in immunoreactive iPFK-2 protein, as measured by Western blotting analysis utilizing a specific anti-iPFK-2 antibody (FIG. 2C). These data demonstrate that iPFK-2, like other genes with AU-rich motifs in their 3'UTR, is induced in primary human monocytes upon pro-inflammatory activation in vitro. In a separate experiment, iPFK-2 expression in peripheral blood leukocytes of 5 HIV-infected patients was examined. In each case, the level of iPFK-2 mRNA was higher than that observed in control, uninfected individuals (n=3). These data suggest that iPFK-2 is induced upon leukocyte activation in vivo.

Figure 3A:
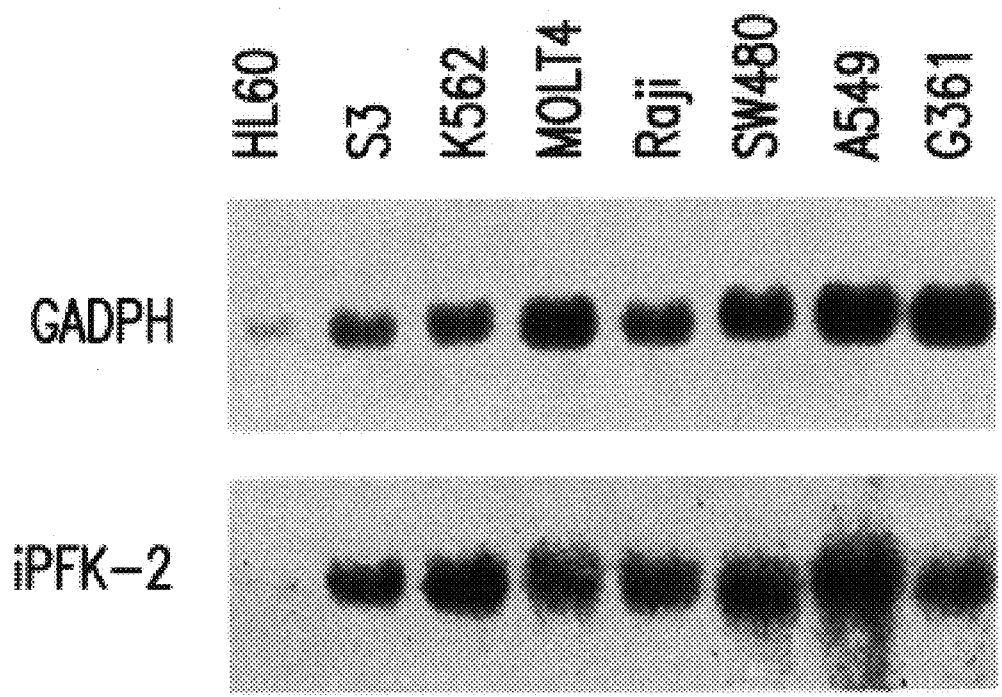
FIGS. 3A–B shows iPFK-2 mRNA expression by human cancer cell lines.
Figure 3B:
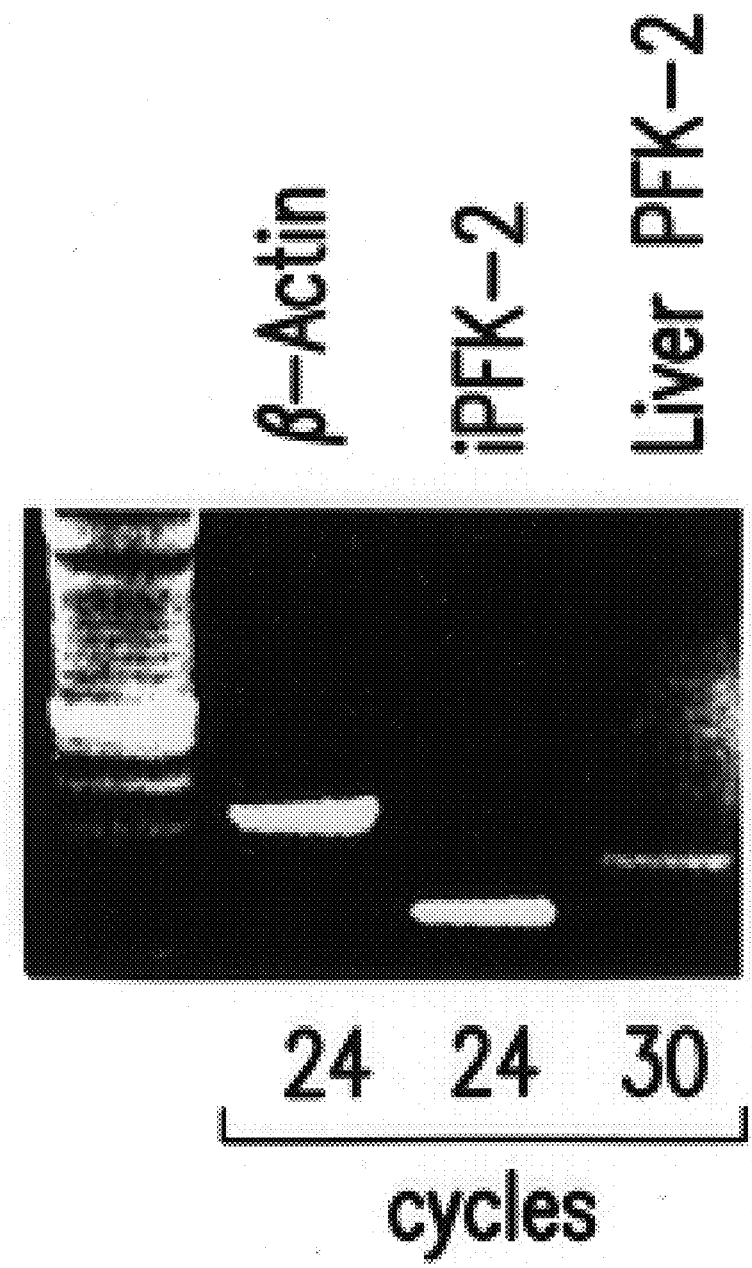

An increase in the level of stable expression of proto-oncogenes with AU-rich 3'UTR's is a characteristic feature of many transformed cells and can be directly oncogenic (Lee et al., *Mol. Cell. Biol.* 8:5521–5527, 1988; Rabbitts et al., *EMBO J.* 4:3727–3733, 1985; and Piechaczyk et al., *Cell* 42:589–597, 1985). Eight human tumor cell lines were examined for iPFK-2 mRNA by Northern blotting and high levels of expression were found (FIG. 3A). The intensities of iPFK-2 hybridization signals were comparable to iPFK-2 signals observed in the RNA obtained from LPS-stimulated primary human monocytes (FIG. 2B). Closer examination of the K562 chronic myelogenous leukemia cell line showed that the expression of iPFK-2 was much higher than that of the hepatic PFK-2 isoform (FIG. 3B). These data suggest that iPFK-2 expression is important in regulating the glycolytic pathway during tumor cell growth.

Figure 4A:
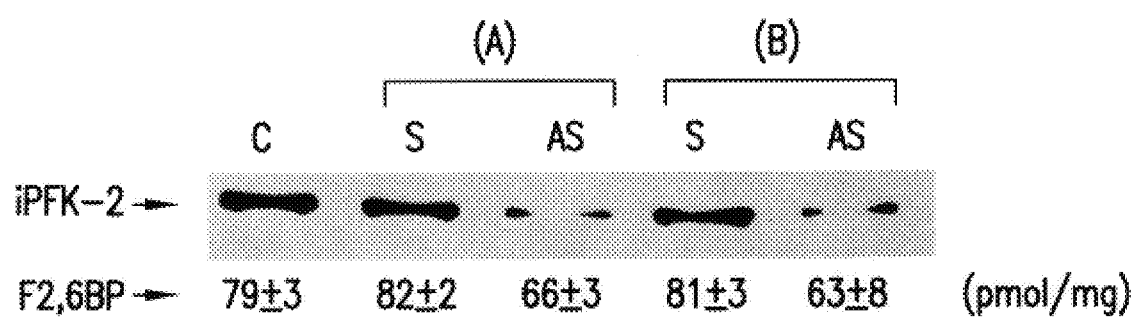
FIGS. 4A–C shows that an iPFK-2 antagonist antisense oligonucleotide inhibited IPFK-2-specific K562 cell proliferation in vitro. Specifically.
Figure 4B:
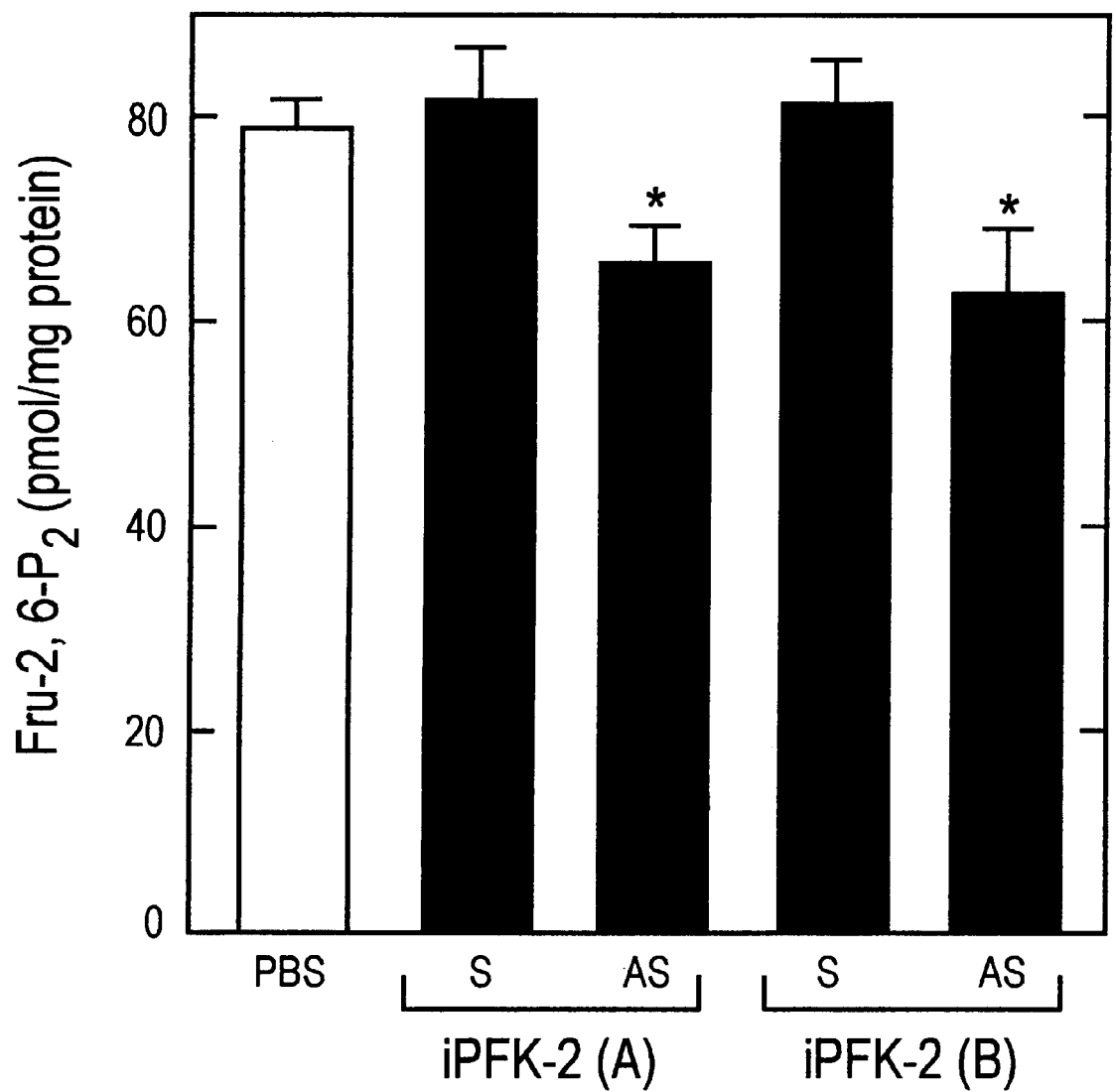

K562 leukemia cells were transfected with iPFK-2-specific anti-sense oligonucleotides. Both iPFK-2 protein and F2,6BP levels were significantly decreased when compared to cells transfected with oligonucleotide controls (FIG. 4A). These data indicate that the kinase activity of iPFK-2 contributes significantly to intracellular F2,6BP levels. The enhanced glycolytic flux in transformed cells facilitates the biosynthesis of 5-phosphoribosyl pyrophosphate (PRPP), a critical precursor for purine and pyrimidine biosynthesis (Eifenbrody et al., *Trends Pharmacol. Sci.* 1:24–245, 1980). Inhibition of iPFK-2 was found to significantly decrease PRPP levels in K562 cells and this decrease was associated with a corresponding decrease in K562 DNA synthesis and cell proliferation (FIG. 4B). A similar level of inhibition of DNA synthesis was observed after the transfection of iPFK-2 anti-sense oligonucleotides into HL-60, MOLT-4, SW480, G361, and KG1A cell lines. These observations indicate that iPFK-2 catalyzed F2-6BP production may enhance glycolytic flux (through stimulation of PFK-1) and permit increased channeling of glucose metabolism in the direction of PRPP synthesis.

Figure 4C:
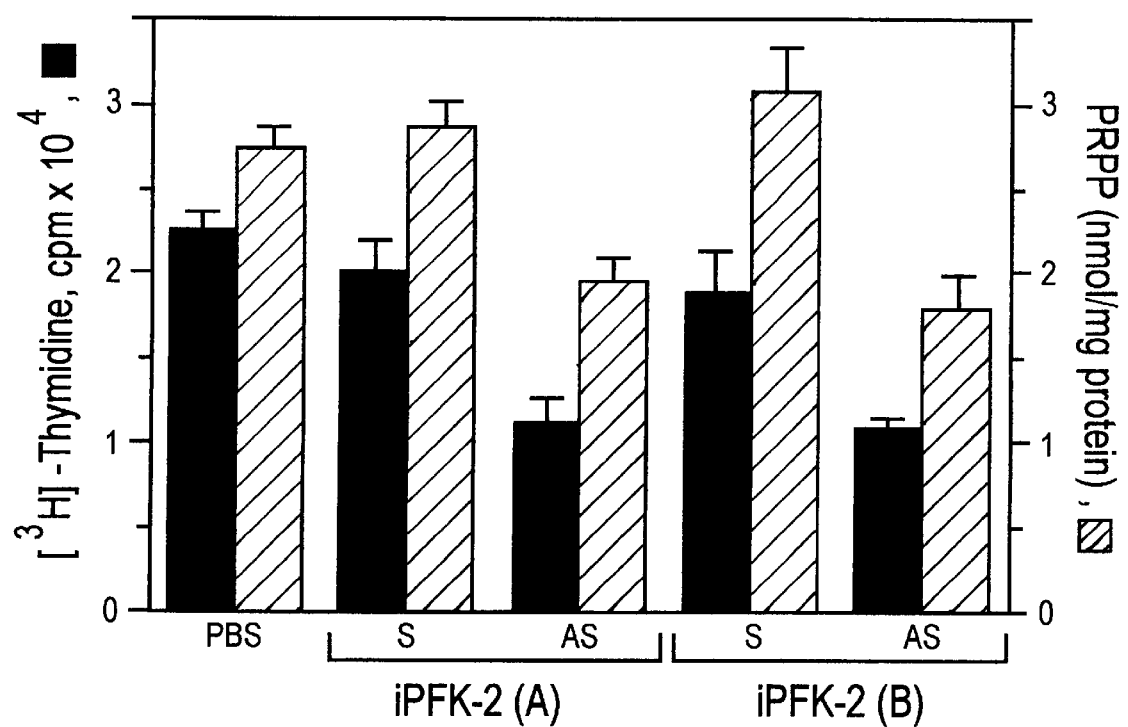

The role of iPFK-2 in tumorigenesis in vivo was examined by administering iPFK-2-specific antisense oligonucleotides to K562 tumor-bearing nude mice. Within 2 days of treatment, tumors for the iPFK-2 antisense-treated mice were significantly smaller than tumors from the iPFK-2 sense oligonucleotide or PBS-treated mice (FIG. 4C).

Procedures and reagents have been developed to test for iPFK-2 inhibitors using rapid in vitro assays suitable for high throughput screening of compounds or libraries of compounds. By homology to known PFK-2 functional domains, the iPFK-2 polypeptide comprises two distinct domains: the amino-terminal portion of the peptide comprises the kinase domain (responsible for phosphorylating fructose 6-phosphate to yield fructose 2,6-bisphosphate) and the carboxy-terminal portion comprises the phosphatase domain (responsible for hydolyzing fructose 2,6-bisphosphate to yield fructose 6-phosphate).

Expression of iPFK2

The complete iPFK2 open reading frame was cloned by screening an EST cDNA library using an iPFK-2 specific probe, and then cloned into the pT7T3D-Pac plasmid (Pharmacia). The sequence of this insert was confirmed as correct by restriction digestion and sequencing. Insert-carrying vector was used to transform bacteria, and positive colonies were detected by performing restriction analysis and sequencing. Finally, the insert was excised and re-cloned into the pET11b expression vector (Novagen) and expressed following the general procedure described below.

Expression of iPFK2 Kinase Domain

The iPFK-2 kinase domain was obtained by PCR cloning. Briefly, a cDNA pool, obtained from reverse transcription of total mRNA of LPS-stimulated human monocytes was used as template for PCR amplification. Two specific primers, containing NdeI and BamHI restriction sites as a 5' extension, were custom synthesized: P1, 5'-ACATATGCCGTTGGAACTGACGCAGAGC-3' [SEQ ID NO. 27], P2, 5'-TGGATCCTCACAGGTAGATGGTACGCGGCT-3' [SEQ ID NO. 28]. The amplified product was found to be at the predicted size and to correspond to the nucleotide sequence of the iPFK-2 kinase domain (corresponding to the positions 47–797 of the iPFK-2 open reading frame). This DNA amplification product was purified with a GENECLEAN® DNA-binding matrix purification kit (BIO101) and then cloned both into the pT7Blue cloning t-vector (Novagen) and into the pET14b expression vector (Novagen), which contains a histidine tag. Insert-carrying clones were detected by PCR screening, and the insert sequence was checked by sequencing. A single pET14b insert-positive colony was inoculated into 2 ml of LB broth and incubated at 37° C. for 3 hours. The bacterial culture was then transferred to a larger flask, containing 100 ml of LB broth, and incubated at 37° C. Once the OD$_{600}$ reached 0.7, the culture was induced by adding IPTG (1 mM), and allowed to grow under shaking overnight at 25° C. Finally, the culture was centrifuged, the supernatant was aspirated and the pellet was frozen to −70° C. These reserved cells were resuspended in lysis buffer (B-PER, Pierce), centrifuged and the supernatant was stored for later use as soluble proteins at −20° C. The kinase domain peptide was purified by using a histidine tag purification kit (Novagen) and tested for its enzymatic activity as described below. This procedure can be used to produce histidine-tagged polypeptides for the kinase domain or the phosphatase domain.

Assay for iPFK2 Kinase Activity

Briefly, the procerue of Sakata et al. (*J. Biol. Chem.* 266: 15764–15770, 1991) was followed. The enzymatic activity of iPFK-2 peptide or the iPFK-2 kinase domain (from natural or recombinant sources) is conveniently assayed by measuring production of the metabolite Fru 2,6BP from Fru 6-P and ATP. One unit of activity is defined as the amount of enzyme that catalyzes the formation of 1 μmol of metabolite per minute. The reaction is conveniently carried out at 30° C. in a final volume of 200 μl, containing 100 mM Tris-HCl, pH7.5, 2 mM DTT, 0.1 mM EDTA, 5 mM ATP, 1 mM F6-P, 5mM potassium phosphate, and 10 mM $MgCl_2$. At timed intervals, 20 μl-aliquots are transferred into 180 μl of 50 mM NaOH, and the diluted solutions are heated to 90° C. to stop the reaction. A suitable aliquot of the heated solutions is assayed for F2,6-BP as described below. Test agents are conveniently evaluated as inhibitors of iPFK-2 kinase activity by inclusion in the above incubation, followed by assay for the production of F2,6BP; control experiments are used to determine that test agents do not themselves interfere with the subsequent fructose 2,6-bisphosphate assay.

Fructose 2,6-bisphosphate Assay

Briefly, the procedure in Van Schaftingen et al. (*Eur. J Biochem.* 129:191–195, 1982) was followed. The F2,6BP assay is conveniently carried out in a 96-well format, at a final volume of 300 μl. In each well, 30 μl enzyme solution (4.5 U/ml aldolase, 17 U/ml glycerol-3-P-dehydrogenase, 50 U/ml triose isomerase, 0.1 U/ml fructose bisphosphate kinase 1-pyrophosphate dependent, in 0.2% BSA) are added to 150 μl of buffer solution (100 mM Tris/acetate buffer, 4 mM magnesium acetate, 100 mM fructose-6-phosphate, in the presence of 0.3 mM NADH). Samples (or standard) (105 μl) are then dispensed into each well, mixing by pipetting. This reaction mixture is incubated at RT for 5 min and then 15 μl of 10 mM pyrophosphate are simultaneously added to each sample and control well, mixing twice by pipetting. The reaction leads to an oxidation of NADH, which is monitored by reading the absorbance of the samples at 1 min intervals for 10 min at 340 nm, yielding OD/min values. The rate of change in absorbance per unit time is a hyperbolic function of the concentration of F2,6BP present in the sample. Experimental values are determined by interpolation of an appropriate standard curve of fructose 2,6 bisphosphate.

EXAMPLE 1

This example illustrates the initial cloning of the iPFK-2 sequence. An expressed sequence tag (EST) containing an AU-rich element was identified in the dbEST database at the National Center for Biotechnology Information by performing a TBLASTN search using the query sequence ATT-TATTTATTTA [SEQ ID NO.: 12]. AU-rich EST (GenBank ID F00287) had been obtained from a Homo sapiens skeletal muscle cDNA library and was unrelated to previously identified sequences. 5'- and 3'-rapid amplification of complementary DNA ends (RACE) was performed using a Human Skeletal Muscle Marathon cDNA-ready RACE kit (Clontech Laboratories, Inc., Palo Alto, Calif.). Gene-specific oligonucleotides used for sequential 5'-directed RACE include 5'-ATTGGTCTGGCAACTGCAAA-3' [SEQ ID NO.: 19], 5'-GATTGTACCATACCTGAAGCACAGCCTC-3' [SEQ ID NO.: 13], 5'-TCTCCTGCCGCTCCAGCTCCATGATCAC-3' [SEQ ID NO.: 14], and 5'-GTCAGCTTCTTGGAGATGTAGGTCTTGC-3' [SEQ ID NO.: 15]. Gene-specific oligonucleotides used for 3'-directed RACE include 5'-TTGGTTTGGGAGCCTCCTATGTGTGACT-3' [SEQ ID NO.: 16] and 5'-TTGGCGTCTACTGATTCCTCCAACTCTC-3' [SEQ ID NO.: 17]. DNA amplification products were purified with a QIAEX® silica gel-based DNA gel extraction kit (Qiagen, Germany) and then cloned into the pT7Blue T-vector (Novagen, Madison, Wis.). For each amplification product, five recombinant clones were isolated and the DNA inserts were sequenced bidirectionally using the Taq DyeDeoxy Terminator Cycle sequencing kit and an ABI Model 373A DNA sequencer (Applied Biosystems, Foster City, Calif.). The entire predicted amino acid sequence of human iPFK-2 is presented in FIG. 1, which shows a comparison against related sequences.

EXAMPLE 2

This example illustrates that LPS induces peripheral blood monocytes to rapidly express iPFK-2 mRNA and protein. PBMCs were isolated by density gradient centrifugation of whole blood through Ficoll (Ficoll-Paque, endotoxin-tested; Pharmacia, Piscataway, N.J.) and then cultured in 6-well plates ($2 \times 10^6$ cells/ml/well RPMI with 10% fetal bovine serum, Hyclone Labs, Logan, Utah). Nonadherent cells were removed by changing the media after 24 hours and the remaining, adherent monocytes were incubated alone as control or in the presence of 1 mg/ml LPS (*E. coli* 0111:B4; Sigma Chemical Co., St. Louis, Mo.). After incubation for 1.5, 3, 6, 12, or 24 hours, cells were lifted, collected by centrifugation at 300 g for 10 min, and immediately analyzed. Total cellular RNA was isolated by a modified guanidinium isothiocyanate method (RNAzol, Cinna Biotecx, Friendswood, Tex.). For RT-PCR analysis, cDNA was prepared from 1.0 mg of total RNA using 0.25 ng of oligo-(dT) and Superscript II following the manufacturer's protocol (Gibco/BRL, Grand Island, N.Y.). Two μl aliquots of cDNA then were amplified by PCR in a Perkin-Elmer model 9600 thermal cycler using the primers listed below and the following cycling program: denaturation for 15 sec at 95° C., annealing for 20 sec at 55° C., and extension for 30 sec at 72° C. for the indicated cycles with a final extension for 5 min at 72° C. The following human mRNA primers were custom synthesized: β-Actin, 5'-TAAGGAGAAGCTGTGCTACG-3' [SEQ ID NO.: 7], 5'-ATCTCCTTCTGCATCCTGTC-3' [SEQ ID NO.: 8]; IL-1β, 5'-CTGTACCTGTCCTGCGTGTT-3' [SEQ ID NO.: 18], 5'-AGCTCTCTTTAGGAAGACAC-3' [SEQ ID NO.: 19]; iPFK-2, 5'-ATTGGTCTGGCAACTGCAAA-3' [SEQ ID NO.: 9], 5'-GGAGCCTCCTATGTGTGACT-3' [SEQ ID NO.: 10]; Liver PFK-2, 5'-GAAGTCAAACTGAATGTGTC-3' [SEQ ID NO.: 20], 5'-CCTCTTGTAGGCAGTAAGTC-3'[SEQ ID NO.: 21] (and 5'-AGGCAGTAAGTCTTTATTCG-3' [SEQ ID NO.: 22], 5'-AAGTCAAACTGCCTGTGTCC-3' [SEQ ID NO.: 23], data not shown) (Gibco/BRL). For Northern blot analysis, RNA (7.5 μg) was electrophoresed through 1.5% agarose-formaldehyde gels, transferred onto nylon membranes (Schleicher & Schuell), and hybridized sequentially with cDNA probes for human iPFK-2 and β-Actin. Probes were produced by PCR using primers described above and then labeled with $^{32}$P by the random-priming method (Megaprime kit, Amersham). Autoradiography was performed at room temperature for 2–6 hr using DuPont Reflection films and intensifying screens. For Western blot analysis, cells were lysed in 2× Laemle sample buffer for 5 min at 95° C. and total cellular proteins were resolved by electrophoresis through 18% SDS polyacrylamide gels under reducing conditions and transferred onto nitrocellulose membranes (Schleicher & Schuell). Membranes were incubated with rabbit polyclonal anti-human iPFK-2 serum (produced by immunization of rabbits with an iPFK-2 carboxy terminal peptide ([NH$_2$]-GQPLLGQACLT-[COOH]) [SEQ ID NO. 24] that was conjugated to KLH. This peptide comprises a unique region of iPFK-2 (amino acids 505–515) that differs from the corresponding portion of placental PFK-2 by a 5 amino acid deletion and 8 amino acid mismatches. Immunoreactive iPFK-2 ($M_r$=59 kD) then was visualized by developing membranes with a donkey peroxidase-conjugated anti-rabbit IgG antibody (1:8,000) followed by reaction with ECL reagents (Amersham International, Buckinghamshire, England) (see FIG. 2).

EXAMPLE 3

This example illustrates iPFK-2 mRNA expression by human cancer cell lines. A Northern blot, containing 2 μg of polyA RNA per lane from 8 different human cell lines (Clontech Labs), was hybridized sequentially with cDNA probes for GADPH (Clontech Labs) and iPFK-2 as in example 2 above. The cell lines were: promyelocytic leukemia HL-60, HeLa cell S3, chronic myelogenous leukemia K562, lymphoblastic leukemia MOLT-4, Burkitt's lymphoma Raji, colorectal adenocarcinoma SW480, lung carcinoma A549, and melanoma G361. For RT-PCR analysis, two μl aliquots of K562 cDNA were amplified by PCR for the indicated cycles in a Perkin-Elmer model 9600 thermal cycler using β-Actin-, iPFK-2, or liver PFK-2-specific primers (primer sequences listed in example 2 above). These data (shown in FIG. 3) show that iPFK-2 is expressed by a large variety of human cancer cell lines and is a predictive tumor marker enzyme sequence that can be used to measure the progress of cancer treatment, to initially identify cells as cancerous or to identify a patient as tumor-bearing.

EXAMPLE 4

This example illustrates that iPFK-2-specific anti-sense oligonucleotides inhibit K562 cell proliferation in vitro. K562 cells (ATCC) in exponential growth phase were cultured in triplicate in 96-well plates (5×10$^3$ cells/well) in RPMI (Gibco/BRL) supplemented with 10% FBS. Cells were incubated with PBS as control or transfected by the lipofectin method (Gibco/BRL) for 20 hours with the following phosphorothioate oligonucleotides: S-iPFK-2 (A) (sense, position 35–55): 5'-AGCCGCGAAGATGCCGTTGG-3' [SEQ ID NO.: 1]; AS-iPFK-2 (A) (anti-sense, position 35–55): 5'-CCAACGGCATCTTCGCGGCT-3' [SEQ ID NO.: 2]; S-IPFK-2 (B) (sense, position 42–62): 5'-AAGATGCCGTTGGAACTGAC-3' [SEQ ID NO.: 3]; AS-iPFK-2 (B) (anti-sense, position 42–62): 5'-GTCAGTTCCAACGGCATCTT-3' [SEQ ID NO.: 4]. Western blot analysis was performed as provided in example 2. Total cellular fructose-2,6-bisphosphate and 5-phosphoribosyl 1-pyrophosphate were measured using the methods described in Van Schaftingen, *Methods. Enz. Anal.* 6:335–341, 1984 and Sant et al., *J. Biol. Biochem.* 16:11038–11045, 1992, respectively. K562 proliferative activity was measured by the incorporation of [$^3$H] thymidine (4 μCi/ml) (DuPont, Boston, Mass.) into DNA over the last 14 hours of incubation/transfection as quantified by liquid scintillation counting. Data in FIG. 4 are expressed as the mean ±SD (n=3). Statistical significance was assessed by two sample T-tests (assuming unequal variances) (*, p<0.05) (Taetle et al., *Cancer Trmt. Reports* 71:297–304, 1987). FIG. 4 shows that a group of antisense oligonucleotides have iPFK-2 antagonist activity and will likely exhibit significant anti-cancer therapeutic activity in view of the widespread prevalence of iPFK-2 and the Warburg effect known for tumor tissue.

EXAMPLE 5

Figure 5:
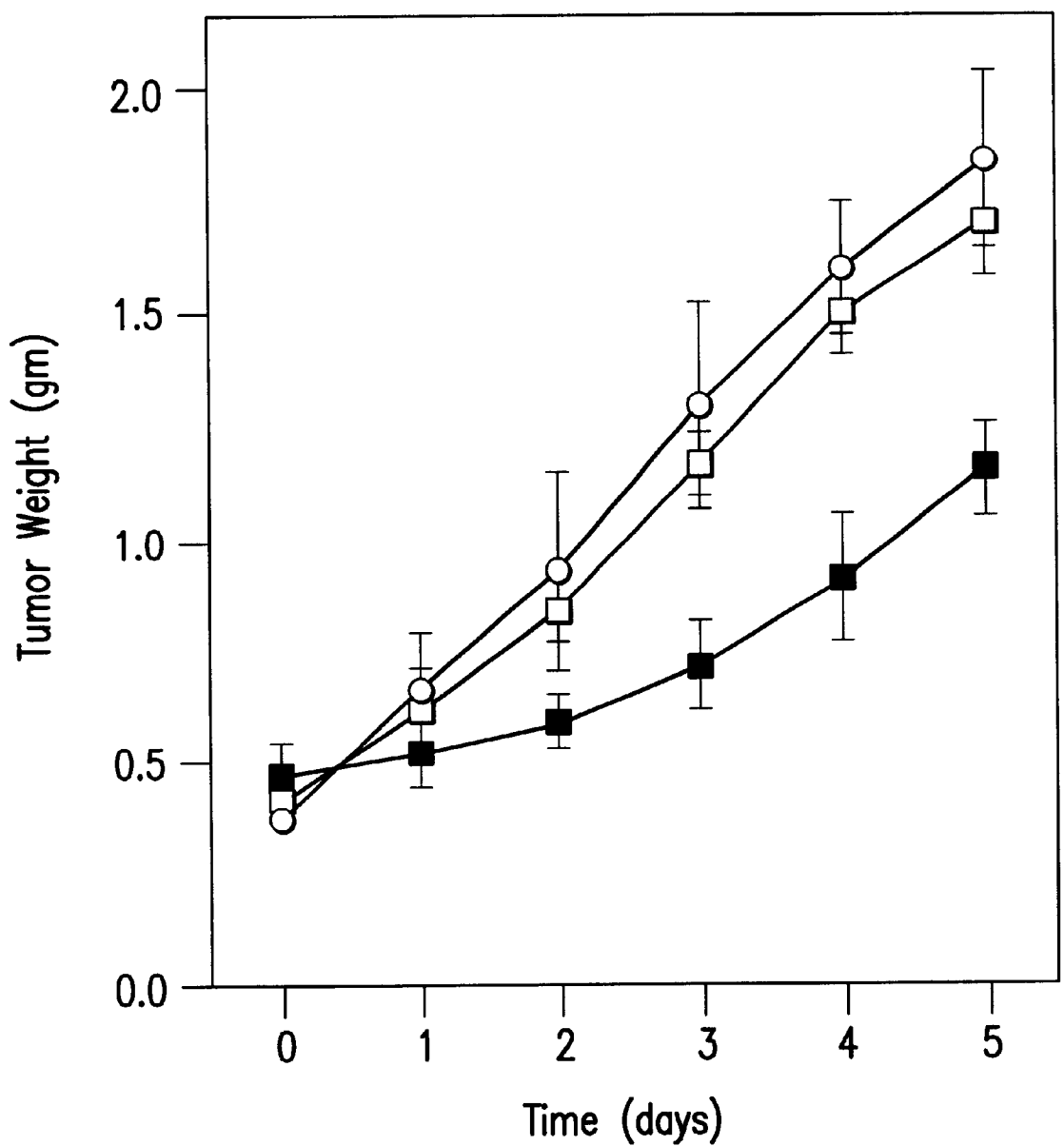
FIG. 5 shows in vivo data providing evidence of iPFK-2 antagonist activity of the antisense oligonucleotides and further showing anti-cancer therapeutic activity of iPFK-2 antagonists.

This example illustrates that iPFK-2-specific anti-sense oligonucleotides inhibit K-562 tumor growth in vivo. K562 tumor-bearing mice were implanted for the indicated days (FIG. 5) with micro-osmotic pumps containing PBS, (○); S-iPFK-2 (B), (□); or AS-iPFK-2 (B), (■). K562 cells were collected from exponential growth phase culture in RPMI medium supplemented with 10% FBS and then washed twice and resuspended in PBS (1×10$^7$ cells/ml). Groups of 5 female BALB/c nude mice (20 gm) (Harlan Labs) were injected s.c. with 0.10 ml of the K562 suspension (1×10$^6$ cells). The tumors were allowed to grow for 7 days to a mean weight of 0.4 gm before treatment was begun. Alzet micro-osmotic pumps (Alza Corporation, Palo Alto, Calif.) loaded with 0.1 ml of PBS or the phosphorothioate oligonucleotides S-iPFK-2 (B) or AS-iPFK-2 (B) (3.0 mM in PBS, see example 4 for sequences) were implanted s.c. into the tumor-bearing mice. Tumor size after 0, 1, 2, 3, and 4 days was determined with Vernier calipers according the following formula: weight (mg)=(width, mm$^2$×length, mm/2) (Taetle et al., *Cancer Trmt. Reports* 71:297–304, 1987). FIG. 5 shows that the antisense oligonucleotides that exhibited iPFK-2 antagonist activity also demonstrate anti-cancer therapeutic activity. Therefore, iPFK-2 antagonists are useful for treating cancers.

EXAMPLE 6

This example illustrates that endotoxemia induces mouse iPFK-2 mRNA expression in spleen and muscle. 10 week-old BALB/c mice (19–20 gm) were injected i.p. with LPS (12.5 mg/kg) or saline as control. After 6 and 24 hours mice were euthanized by CO$_2$ asphyxiation and the brain, liver, lower extremity muscles, and spleen were removed by dissection. Total RNA extraction and Northern blot analysis were performed as above using a mouse iPFK-2-specific cDNA probe (amplified from mouse peritoneal macrophage cDNA by 30 cycle RT-PCR using the following human iPFK-2-specific primers: 5'-TGAGGCAGACGTGTCGGTTC-3' [SEQ ID NO.: 25], 5'-CAGCAGCTCCAGGAAAGTGT-3' [SEQ ID NO.: 26]).

Figure 6:
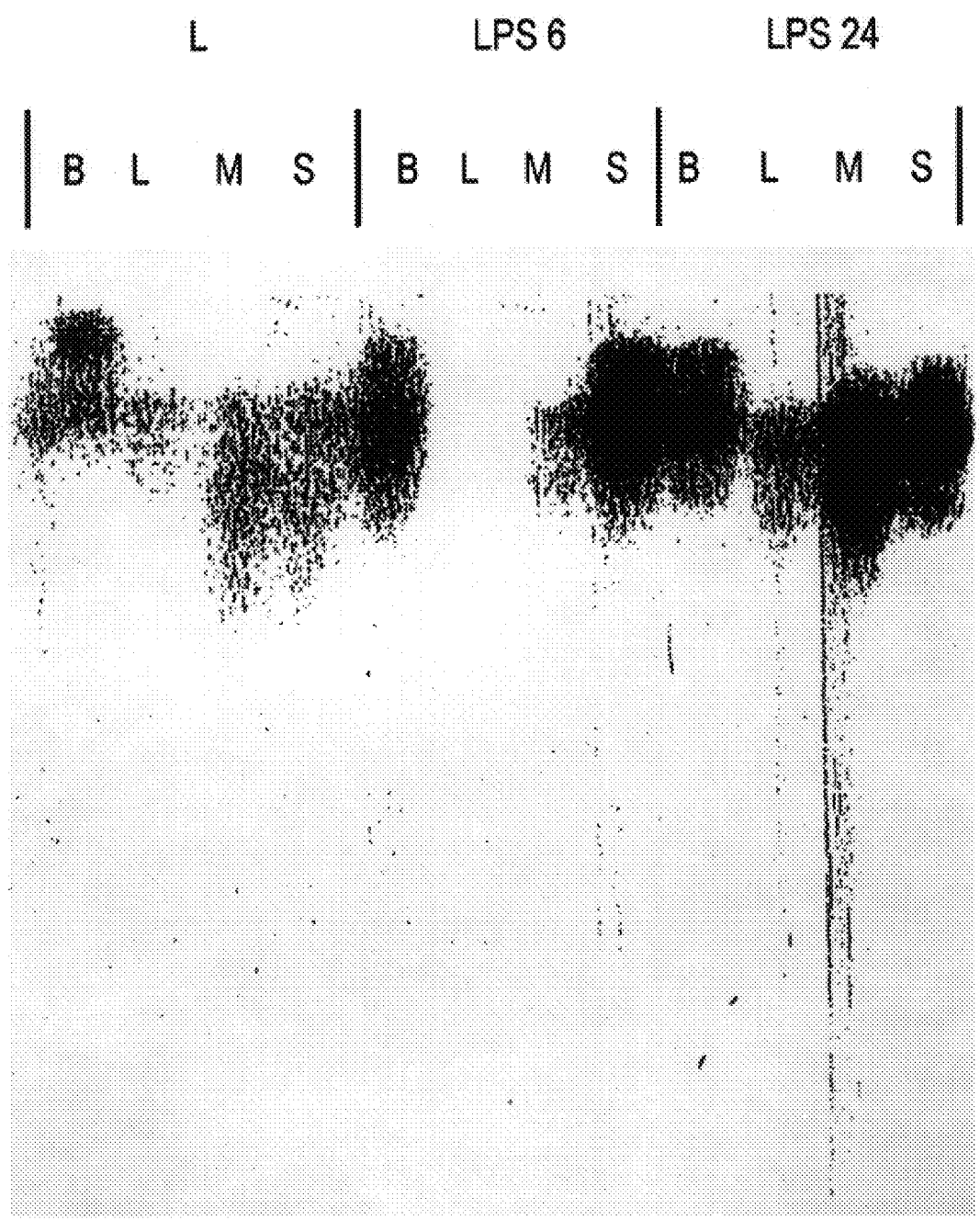
FIG. 6 shows that in vivo endotoxemia induces mouse iPFK-2 mRNA expression in spleen and muscle tissue. 10 week-old BALB/c mice (19–20 gm) were injected i.p. with LPS (12.5 mg/kg) or saline as control. After 6 and 24 hours mice were euthanized by $CO_2$ asphyxiation and the brain, liver, lower extremity muscles, and spleen were removed by dissection. Total RNA extraction and Northern blot analysis were performed using a mouse iPFK-2-specific cDNA probe (amplified from mouse peritoneal macrophage cDNA by 30 cycle RT-PCR using the following human iPFK-2-specific primers: 5'-TGAGGCAGACGTGTCGGTTC-3' [SEQ ID NO.: 5], 5'-CAGCAGCTCCAGGAAAGTGT-3' [SEQ ID NO.: 6]. These in vivo data show that LPS induced iPFK-2 mRNA expression in mice in brain, liver, muscle and spleen tissues.

The results are presented in FIG. 6 and show that LPS induced iPFK-2 mRNA expression in mouse tissues. These data illustrate the predictive pharmacologic importance of iPFK-2 as a therapeutic marker for inflammatory conditions.

EXAMPLE 7

This example illustrates that iPFK-2 is overexpressed in peripheral blood mononuclear cells (PBMCs) of HIV+ individuals. Total RNA was isolated from 3 uninfected individuals (lanes 1–3) and 5 HIV+ individuals (lanes 4–8) and analyzed by RT-PCR with β-Actin-specific primers (5'-TAAGGAGAAGCTGTGCTACG-3' [SEQ ID NO.: 7], 5'-ATCTCCTTCTGCATCCTGTC-3' [SEQ ID NO.: 8], 19 cycles) and iPFK-2-specific primers (5'-ATTGGTCTGGCAACTGCAAA-3' [SEQ ID NO.: 9], 5'-GGAGCCTCCTATGTGTGACT-3' [SEQ ID NO.: 10], 23 cycles).

Figure 7:
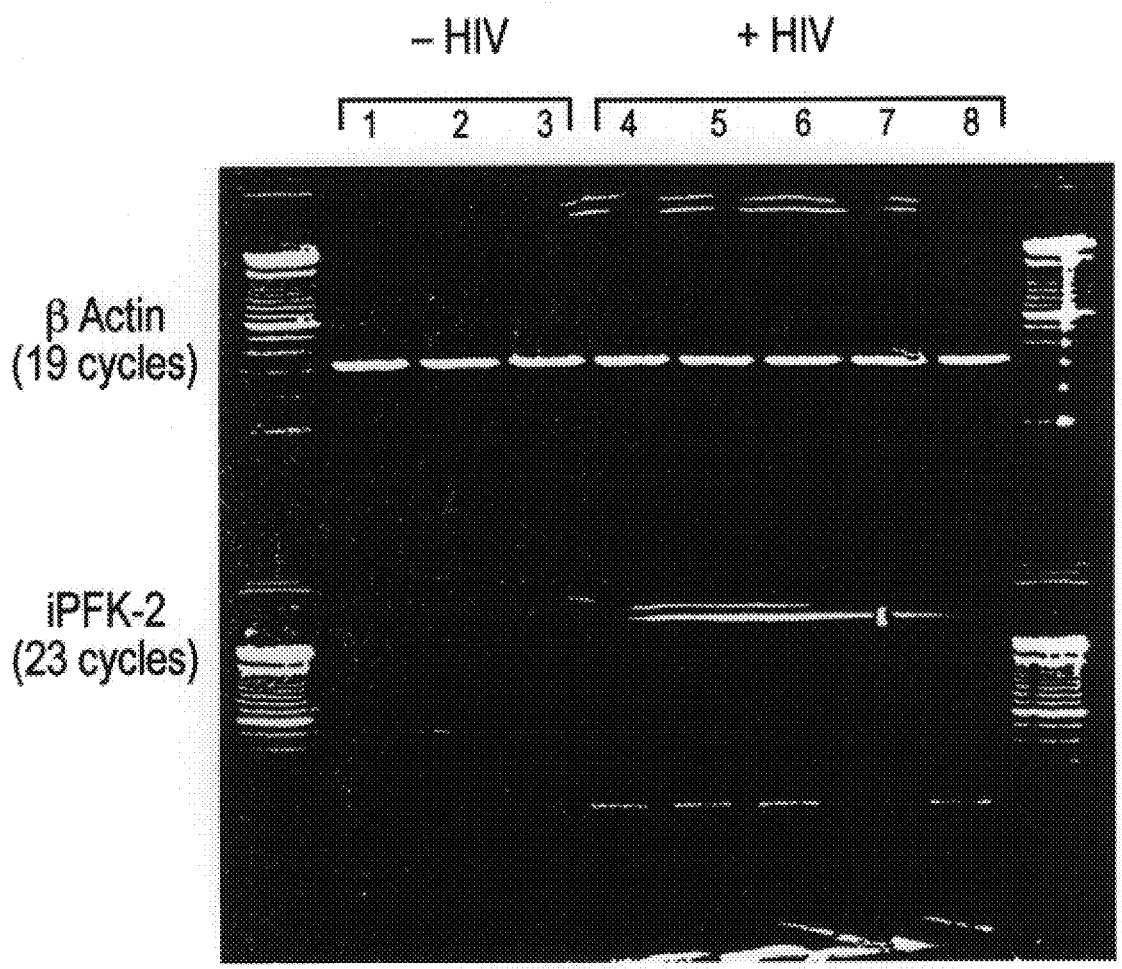
FIG. 7 shows that iPFK-2 is overexpressed in PBMCs (peripheral blood mononuclear cells) of HIV+ individuals. Total RNA was isolated from 3 uninfected individuals (lanes 1–3) and 5 HIV+ individuals (lanes 4–8) and analyzed by RT-PCR with β-Actin-specific primers (5'-TAAGGAGAAGCTGTGCTACG-3' [SEQ ID NO.: 7], 5'-ATCTCCTTCTGCATCCTGTC-3' [SEQ ID NO.: 8], 19 cycles) and iPFK-2-specific primers (5'-ATTGGTCTGGCAACTGCAAA-3' [SEQ ID NO.: 9], 5'-GGAGCCTCCTATGTGTGACT-3' [SEQ ID NO.: 10], 23 cycles).
Figure 8:
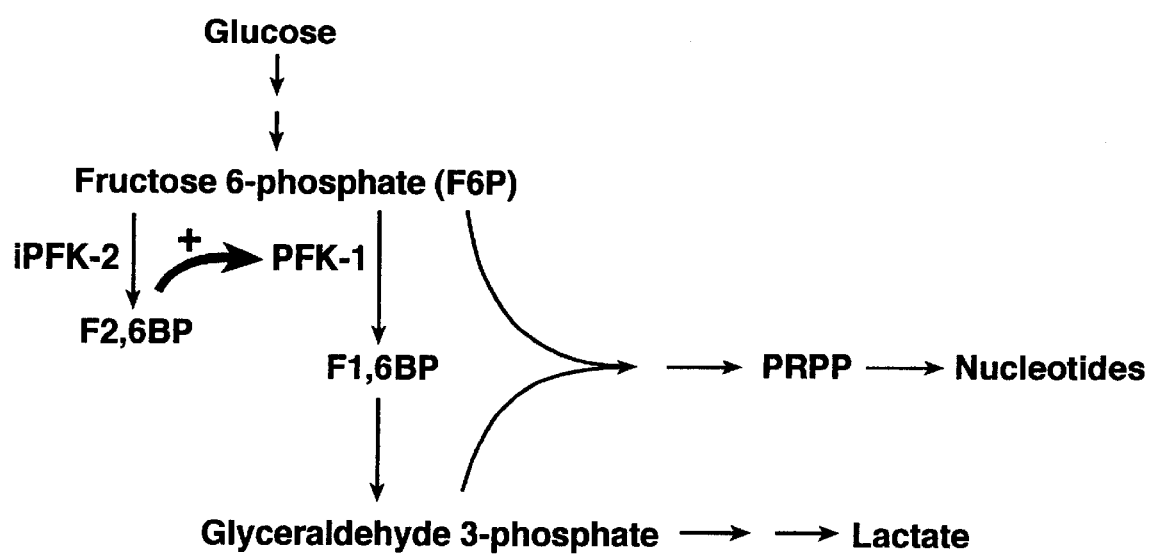
FIG. 8 shows a postulated metabolic scheme for the metabolic role of iPFK-2, particularly in rapidly dividing cancer cells where there is a buildup of lactate from anaerobic metabolism and production of nucleotides to support rapid cell division.

The results are presented in FIG. 7, and show that iPFK-2 is over-expressed in PBMCs from HIV+ individuals.

EXAMPLE 8

This example illustrates anti-tumor therapeutic activity of iPFK-2 antagonists. Test compounds, such as the potential iPFK-2 antagonist 2,5-anhydro-D-mannitol are conveniently tested for inhibition of iPFK-2 enzymatic (i.e., kinase) activity using recombinant iPFK-2 polypeptide as provided herein. 2,5-anhydro-D-mannitol, or other test compounds may then be further tested in an in vitro assay of anti-tumor therapeutic activity that correlates iPFK-2 inhibition of iPFK-2 kinase enzymatic activity with therapeutic anti-tumor pharmacologic activity. K562 tumor cells ($1\times10^4$ cells grown in RPMI supplemented with 10% FBS) are exposed to different concentrations of 2,5-anhydro-D-mannitol or other test compounds and control sugar (glucose) for 12 hours. A cell proliferation assay, for instance, measuring tritiated thymidine uptake, is then used to estimate tumor cell proliferation. Thus, this procedure helps to determine if a test compound is an iPFK-2 antagonist, wherein an antagonist is an agent that acts on iPFK-2 to decrease F2,6 P and/or increase F6P in the assay.

Figure 9:
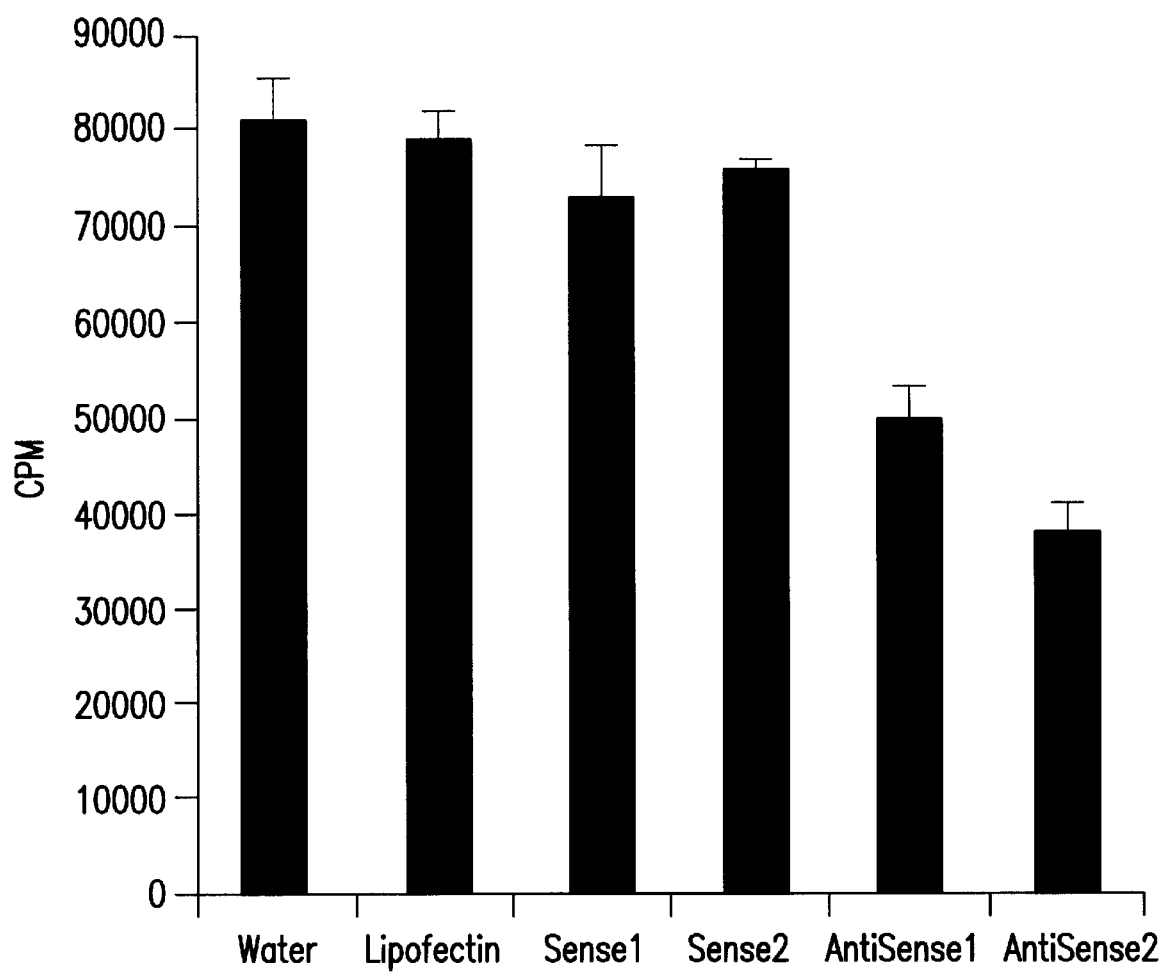
FIG. 9 shows the results of iPFK-2 antisense oligonucleotides inhibiting the proliferation of T cell tumor line MOLT-4. Two different iPFK-2 antisense oligonucleotides were effective and exhibited pharmacologic anti-tumor activity in this predictive assay.

A further tumor cell proliferation assay was also conducted, as described in example 4, with two different iPFK-2 antisense oligonuclotides using the T cell tumor cell line MOLT-4. As shown in FIG. 9, both antisense oligonucleotides inhibited tumor cell proliferation and exhibited anti-tumor therapeutic activity in this predictive in vitro assay.

We claim:

1. A method for screening for a candidate therapeutic agent that inhibits kinase enzymatic activity of iPFK-2, comprising:
   (a) expressing an iPFK-2 enzyme or kinase domain thereof from the cDNA sequence of SEQ ID NO. 11;
   (b) purifying and isolating the expressed iPFK-2 enzyme or kinase domain thereof;
   (c) providing a test compound that is a candidate therapeutic agent and fructose 6-phosphate substrate; and
   (d) measuring formation of fructose 2,6-bisphosphate product as a measure of the kinase enzymatic activity, wherein a reduction of kinase enzymatic activity compared to a control assay that does not include said test compound identifies a candidate therapeutic agent.

2. The method of claim 1 further comprising the step of determining that the candidate therapeutic agent does not inhibit the kinase enzymatic activity of liver of PFK-2.

* * * * *

```
                          SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
         (A) LENGTH: 20
         (B) TYPE: nucleic acid
         (C) STRANDEDNESS: single
         (D) TOPOLOGY: unknown (ii) MOLECULE TYPE: hiPFK-2 antisense (xi) SEQUENCE DESCRIPTION: SEQ ID NO: 1:

AGCCGCGAAG ATGCCGTTGG                                              20

(2) INFORMATION FOR SEQ ID NO: 2:

(i) SEQUENCE CHARACTERISTICS:
         (A) LENGTH: 20
         (B) TYPE: nucleic acid
         (C) STRANDEDNESS: single
         (D) TOPOLOGY: unknown (ii) MOLECULE TYPE: hiPFK-2 antisense (xi) SEQUENCE DESCRIPTION: SEQ ID NO: 2:

CCAACGGCAT CTTCGCGGCT                                              20

(2) INFORMATION FOR SEQ ID NO: 3:

(i) SEQUENCE CHARACTERISTICS:
         (A) LENGTH: 20
         (B) TYPE: nucleic acid
         (C) STRANDEDNESS: single
         (D) TOPOLOGY: unknown (ii) MOLECULE TYPE: hiPFK-2 antisense (xi) SEQUENCE DESCRIPTION: SEQ ID NO: 3:

AAGATGCCGT TGGAACTGAC                                              20
```

(2) INFORMATION FOR SEQ ID NO: 4:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: hiPFK-2 antisense (xi) SEQUENCE DESCRIPTION: SEQ ID NO: 4:

```
GTCAGTTCCA ACGGCATCTT                                              20
```

(2) INFORMATION FOR SEQ ID NO: 5:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 5:

```
TGAGGCAGAC GTGTCGGTTC                                              20
```

(2) INFORMATION FOR SEQ ID NO: 6:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 6:

```
CAGCAGCTCC AGGAAAGTGT                                              20
```

(2) INFORMATION FOR SEQ ID NO: 7:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 7:

```
TAAGGAGAAG CTGTGCTACG                                              20
```

(2) INFORMATION FOR SEQ ID NO: 8:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 8:

```
ATCTCCTTCT GCATCCTGTC                                              20
```

(2) INFORMATION FOR SEQ ID NO: 9:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 9:

```
ATTGGTCTGG CAACTGCAAA                                                  20
```

(2) INFORMATION FOR SEQ ID NO: 10:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 10:

```
GGAGCCTCCT ATGTGTGACT                                                  20
```

(2) INFORMATION FOR SEQ ID NO: 11:

(i) SEQUENCE CHARACTERISTICS:
        (A) LENGTH: 4220 base pairs
        (B) TYPE: nucleic acid
        (C) STRANDEDNESS: single
        (D) TOPOLOGY: unknown (ii) MOLECULE TYPE: human iPFK-2

(xi) SEQUENCE DESCRIPTION: SEQ ID NO: 11:

```
CAGGTCGAGC GGCAGGGCCT GGTGGCGAGA GCGCAGCCGC GAAGATGCCG                  50

TTGGAACTGA CGCAGAGCCG AGTGCAGAAG ATCTGGGTGC CCGTGGACCA                 100

CAGGCCCTCG TTGCCCAGAT CCTGTGGGCC AAAGCTGACC AACTCCCCCA                 150

CCGTCATCGT CATGGTGGGC CTCCCCGCCC GGGGCAAGAC CTACATCTCC                 200

AAGAAGCTGA CTCGCTACCT CAACTGGATT GGCGTCCCCA CAAAAGTGTT                 250

CAACGTCGGG GAGTATCGCC GGGAGGCTGT GAAGCAGTAC AGCTCCTACA                 300

ACTTCTTCCG CCCCGACAAT GAGGAAGCCA TGAAAGTCCG GAAGCAATGT                 350

GCCCTAGCTG CCTTGAGAGA TGTCAAAAGC TACCTGGCGA AGAAGGGGG                  400

ACAAATTGCG GTTTTCGATG CCACCAATAC TACTAGAGAG AGGAGACACA                 450

TGATCCTCCA TTTTGGCAAA GAAAATGACT TTAAGGCGTT TTTCATCGAG                 500

TCGGTGTGCG ACGACCCTAC AGTTGTGGCC TCCAATATCA TGGAAGTTAA                 550

AATCTCCAGC CCGGATTACA AAGACTGCAA CTCGGCAGAA GCCATGGACG                 600

ACTTCATGAA GAGGATCAGT TGCTATGAAG CCAGCTACCA GCCCCTCGAC                 650

CCCGACAAAT GCGACAGGGA CTTGTCGCTG ATCAAGGTGA TTGACGTGGG                 700

CCGGAGGTTC CTGGTGAACC GGGTGCAGGA CCACATCCAG AGCCGCATCG                 750

TGTACTACCT GATGAACATC CACGTGCAGC CGCGTACCAT CTACCTGTGC                 800

CGGCACGGCG AGAACGAGCA CAACCTCCAG GGCCGCATCG GGGCGACTC                  850

AGGCCTGTCC AGCCGGGGCA AGAAGTTTGC CAGTGCTCTG AGCAAGTTCG                 900

TGGAGGAGCA GAACCTGAAG GACCTGCGCG TGTGGACCAG CCAGCTGAAG                 950
```

```
                                             -continued

AGCACCATCC AGACGGCCGA GGCGCTGCGG CTGCCCTACG AGCAGTGGAA         1000

GGCGCTCAAT GAGATCGACG CGGGCGTCTG TGAGGAGCTG ACCTACGAGG         1050

AGATCAGGGA CACCTACCCT GAGGAGTATG CGCTGCGGGA GCAGGACAAG         1100

TACTATTACC GCTACCCCAC CGGGGAGTCC TACCAGGACC TGGTCCAGCG         1150

CTTGGAGCCA GTGATCATGG AGCTGGAGCG GCAGGAGAAT GTGCTGGTCA         1200

TCTGCCACCA GGCCGTCCTG CGCTGCCTGC TTGCCTACTT CCTGGATAAG         1250

AGTGCAGAGG AGATGCCCTA CCTGAAATGC CCTCTTCACA CCGTCCTGAA         1300

ACTGACGCCT GTCGCTTATG GCTGCCGTGT GGAATCCATC TACCTGAACG         1350

TGGAGTCCGT CTGCACACAC CGGGAGAGGT CAGAGGATGC AAAGAAGGGA         1400

CCTAACCCGC TCATGAGACG CAATAGTGTC ACCCCGCTAG CCAGCCCCGA         1450

ACCCACCAAA AAGCCTCGCA TCAACAGCTT TGAGGAGCAT GTGGCCTCCA         1500

CCTCGGCCGC CCTGCCCAGC TGCCTGCCCC CGGAGGTGCC CACGCAGCTG         1550

CCTGGACAAC CTTTGCTAGG GCAAGCCTGT CTAACATGAA AGGTTCCCGG         1600

AGCAGCGCTG ACTCCTCCAG GAAACACTGA GGCAGACGTG TCGGTTCCAT         1650

TCCATTTCCA TTTCTGCAGC TTAGCTTGTG TCCTGCCCTC CGCCCGAGGC         1700

AAAACGTATC CTGAGGACTT CTTCCGGAGA GGGTGGGGTG GAGCAGCGGG         1750

GGAGCCTTGG CCGAAGAGAA CCATGCTTGG CACCGTCTGT GTCCCCTCGG         1800

CCGCTGGACA CCAGAAAGCC ACGTGGGTCC CTGGCGCCCT GCCTTTAGCC         1850

GTGGGGCCCC CACCTCCACT CTCTGGGTTT CCTAGGAATG TCCAGCCTCG         1900

GAGACCTTCA CAAAGCCTTG GGAGGGTGAT GAGTGCTGGT CCTGACAAGA         1950

GGCCGCTGGG GACACTGTGC TGTTTTGTTT CGTTTCTGTG ATCTCCCGGC         2000

ACGTTTGGAG CTGGGAAGAC CACACTGGTG GCAGAATCCT AAAATTAAAG         2050

GAGGCAGGCT CCTAGTTGCT GAAAGTTAAG GAATGTGTAA AACCTCCACG         2100

TGACTGTTTG GTGCATCTTG ACCTGGGAAG ACGCCTCATG GGAACGAACT         2150

TGGACAGGTG TTGGGTTGAG GCCTCTTCTG CAGGAAGTCC CTGAGCTGAG         2200

ACGCAAGTTG GCTGGGTGGT CCGCACCCTG GCTCTCCTGC AGGTCCACAC         2250

ACCTTCCAGG CCTGTGGCCT GCCTCCAAAG ATGTGCAAGG GCAGGCTGGC         2300

TGCACGGGGA GAGGGAAGTA TTTTGCCGAA ATATGAGAAC TGGGGCCTCC         2350

TGCTCCCAGG GAGCTCCAGG GCCCCTCTCT CCTCCCACCT GGACTTGGGG         2400

GGAACTGAGA AACACTTTCC TGGAGCTGCT GGCTTTTGCA CTTTTTTGAT         2450

GGCAGAAGTG TGACCTGAGA GTCCCACCTT CTCTTCAGGA ACGTAGATGT         2500

TGGGGTGTCT TGCCCTGGGG GCTTGGAAC CTCTGAAGGT GGGGAGCGGA          2550

ACACCTGGCA TCCTTCCCCA GCACTTGCAT TACCGTCCCT GCTCTTCCCA         2600

GGTGGGGACA GTGGCCCAAG CAAGGCCTCA CTCGCAGCCA CTTCTTCAAG         2650

AGCTGCCTGC ACACTGTCTT GGAGCATCTG CCTTGTGCCT GGCACTCTGC         2700

CGGTGCCTTG GGAAGGTCGG AAGAGTGGAC TTTGTCCTGG CCTTCCCTTC         2750

ATGGCGTCTA TGACACTTTT GTGGTGATGG AAAGCATGGG ACCTGTCGTC         2800

TCAGCCTGTT GGTTTCTCCT CATTGCCTCA ACCCTGGGG TAGGTGGGAC          2850

GGGGGGTCTC GTGCCCAGAT GAAACCATTT GGAAACTCGG CAGCAGAGTT         2900

TGTCCAAATG ACCCTTTTCA GGATGTCTCA AAGCTTGTGC CAAAGGTCAC         2950
```

| | |
|---|---|
| TTTTCTTTCC TGCCTTCTGC TGTGAGCCCT GAGATCCTCC TCCCAGCTCA | 3000 |
| AGGGACAGGT CCTGGGTGAG GGTGGGAGAT TTAGACACCT GAAACTGGGC | 3050 |
| GTGGAGAGAA GAGCCGTTGC TGTTTGTTTT TTGGGAAGAG CTTTTAAAGA | 3100 |
| ATGCATGTTT TTTTCCTGGT TGGAATTGAG TAGGAACTGA GGCTGTGCTT | 3150 |
| CAGGTATGGT ACAATCAAGT GGGGGATTTT CATGCTGAAC CATTCAAGCC | 3200 |
| CTCCCCGCCC GTTGCACCCA CTTTGGCTGG CGTCTGCTGG AGAGGATGTC | 3250 |
| TCTGTCCGCA TTCCCGTGCA GCTCCAGGCT CGCGCAGTTT TCTCTCTCCC | 3300 |
| CCTGGATGTT GAGTCTCATC AGAATATGTG GGTAGGGGGT GGACGTGCAC | 3350 |
| GGGTGCATGA TTGTGCTTAA CTTGGTTGTA TTTTTCGATT TGACATGGAA | 3400 |
| GGCCTGTTGC TTTGCTCTTG AGAATAGTTT CTCGTGTCCC CCTCGCAGGC | 3450 |
| CTCATTCTTT GAACATCGAC TCTGAAGTTT GATACAGATA GGGGCTTGAT | 3500 |
| AGCTGTGGTC CCCCTCTCCC CTCTGACTAC CTAAAATCAA TACCTAAATA | 3550 |
| CAGAAGCCTT GGTCTAACAC GGGACTTTTA GTTTGCGAAG GGCCTAGATA | 3600 |
| GGGAGAGAGG TAACATGAAT CTGGACAGGG AGGGAGATAC TATAGAAAGG | 3650 |
| AGAACACTGC CTACTTTGCA AGCCAGTGAC CTGCCTTTTG AGGGGACATT | 3700 |
| GGACGGGGGC CGGGGCGGG GGTTGGGTTT GAGCTACAGT CATGAACTTT | 3750 |
| TGGCGTCTAC TGATTCCTCC AACTCTCCAC CCCACAAAAT AACGGGGACC | 3800 |
| AATATTTTA ACTTTGCCTA TTTGTTTTTG GGTGAGTTTC CCCCCTCCTT | 3850 |
| ATTCTGTCCT GAGACCACGG GCAAAGCTCT TCATTTTGAG AGAGAAGAAA | 3900 |
| AACTGTTTGG AACCACACCA ATGATATTTT TCTTTGTAAT ACTTGAAATT | 3950 |
| TATTTTTTA TTATTTTGAT AGCAGATGTG CTATTTATTT ATTTAATATG | 4000 |
| TATAAGGAGC CTAAACAATA GAAAGCTGTA GAGATTGGGT TTCATTGTTA | 4050 |
| ATTGGTTTGG GAGCCTCCTA TGTGTGACTT ATGACTTCTC TGTGTTCTGT | 4100 |
| GTATTTGTCT GAATTAATGA CCTGGGATAT AAAGCTATGC TAGCTTTCAA | 4150 |
| ACAGGAGATG CCTTTCAGAA ATTTGTATAT TTTGCAGTTG CCAGACCAAT | 4200 |
| AAAATACCTG GTTGAAATAC | 4220 |

(2) INFORMATION FOR SEQ ID NO: 12:

(i) SEQUENCE CHARACTERISTICS:
        (A) LENGTH: 13
        (B) TYPE: nucleic acid
        (C) STRANDEDNESS: single
        (D) TOPOLOGY: unknown (ii) MOLECULE TYPE: query sequence (xi) SEQUENCE DESCRIPTION: SEQ ID NO: 12:

| | |
|---|---|
| ATTTATTTAT TTA | 13 |

(2) INFORMATION FOR SEQ ID NO: 13:

(i) SEQUENCE CHARACTERISTICS:
        (A) LENGTH: 28
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 13:

GATTGTACCA TACCTGAAGC ACAGCCTC                                           28

(2) INFORMATION FOR SEQ ID NO: 14:

(i) SEQUENCE CHARACTERISTICS:
            (A) LENGTH: 28
            (B) TYPE: nucleic acid
            (C) STRANDEDNESS: single
            (D) TOPOLOGY: unknown (ii) MOLECULE TYPE: PCR primer (xi) SEQUENCE DESCRIPTION: SEQ ID NO: 14:

TCTCCTGCCG CTCCAGCTCC ATGATCAC                                           28

(2) INFORMATION FOR SEQ ID NO: 15:

(i) SEQUENCE CHARACTERISTICS:
            (A) LENGTH: 28
            (B) TYPE: nucleic acid
            (C) STRANDEDNESS: single
            (D) TOPOLOGY: unknown (ii) MOLECULE TYPE: PCR primer (xi) SEQUENCE DESCRIPTION: SEQ ID NO: 15:

GTCAGCTTCT TGGAGATGTA GGTCTTGC                                           28

(2) INFORMATION FOR SEQ ID NO: 16:

(i) SEQUENCE CHARACTERISTICS:
            (A) LENGTH: 28
            (B) TYPE: nucleic acid
            (C) STRANDEDNESS: single
            (D) TOPOLOGY: unknown (ii) MOLECULE TYPE: PCR primer (xi) SEQUENCE DESCRIPTION: SEQ ID NO: 16:

TTGGTTTGGG AGCCTCCTAT GTGTGACT                                           28

(2) INFORMATION FOR SEQ ID NO: 17:

(i) SEQUENCE CHARACTERISTICS:
            (A) LENGTH: 28
            (B) TYPE: nucleic acid
            (C) STRANDEDNESS: single
            (D) TOPOLOGY: unknown (ii) MOLECULE TYPE: PCR primer (xi) SEQUENCE DESCRIPTION: SEQ ID NO: 17:

TTGGCGTCTA CTGATTCCTC CAACTCTC                                           28

(2) INFORMATION FOR SEQ ID NO: 18:

(i) SEQUENCE CHARACTERISTICS:
            (A) LENGTH: 20
            (B) TYPE: nucleic acid
            (C) STRANDEDNESS: single
            (D) TOPOLOGY: unknown (ii) MOLECULE TYPE: PCR primer (xi) SEQUENCE DESCRIPTION: SEQ ID NO: 18:

CTGTACCTGT CCTGCGTGTT                                                    20

(2) INFORMATION FOR SEQ ID NO: 19:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 19:

AGCTCTCTTT AGGAAGACAC    20

(2) INFORMATION FOR SEQ ID NO: 20:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 20:

GAAGTCAAAC TGAATGTGTC    20

(2) INFORMATION FOR SEQ ID NO: 21:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 21:

CCTCTTGTAG GCAGTAAGTC    20

(2) INFORMATION FOR SEQ ID NO: 22:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 22:

AGGCAGTAAG TCTTTATTCG    20

(2) INFORMATION FOR SEQ ID NO: 23:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 23:

AAGTCAAACT GCCTGTGTCC    20

(2) INFORMATION FOR SEQ ID NO: 24:

(i) SEQUENCE CHARACTERISTICS:
        (A) LENGTH: 11
        (B) TYPE: amino acid
        (C) STRANDEDNESS: single
        (D) TOPOLOGY: unknown (ii) MOLECULE TYPE: polypeptide (xi) SEQUENCE DESCRIPTION: SEQ ID NO: 24:

Gly Gln Pro Leu Leu Gly Gln Ala Cys Leu Thr
               5                 10

(2) INFORMATION FOR SEQ ID NO: 25:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 25:

TGAGGCAGAC GTGTCGGTTC                                            20

(2) INFORMATION FOR SEQ ID NO: 26:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 26:

CAGCAGCTCC AGGAAAGTGT                                            20

(2) INFORMATION FOR SEQ ID NO: 27:

(i) SEQUENCE CHARACTERISTICS:
        (A) LENGTH: 28
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 27:

ACATATGCCG TTGGAACTGA CGCAGAGC                                28

(2) INFORMATION FOR SEQ ID NO: 28:

(i) SEQUENCE CHARACTERISTICS:
        (A) LENGTH: 30
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO: 28:

TGGATCCTCA CAGGTAGATG GTACGCGGCT                            30